(12) United States Patent
Schilling et al.

(10) Patent No.: US 11,642,512 B2
(45) Date of Patent: May 9, 2023

(54) MANAGING THE ELECTRIC FIELD EXPOSURE IN A FULLY IMPLANTED LVAD SYSTEM

(71) Applicant: Medtronic, Inc., Minneapolis, MN (US)

(72) Inventors: Eric A. Schilling, Ham Lake, MN (US); David J. Peichel, Minneapolis, MN (US); Jason C. Lee, Edina, MN (US); David I. Siegfried, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 331 days.

(21) Appl. No.: 17/001,969

(22) Filed: Aug. 25, 2020

(65) Prior Publication Data
US 2022/0062515 A1 Mar. 3, 2022

(51) Int. Cl.
*A61M 60/873* (2021.01)
*A61M 60/875* (2021.01)
*A61M 60/871* (2021.01)
*A61M 60/148* (2021.01)

(52) U.S. Cl.
CPC ........ *A61M 60/871* (2021.01); *A61M 60/148* (2021.01); *A61M 2205/18* (2013.01); *A61M 2205/52* (2013.01); *A61M 2205/8206* (2013.01)

(58) Field of Classification Search
CPC .. A61M 2205/8243; A61M 2205/8206; A61M 2205/3538; A61M 2205/3523; A61M 2205/8237; A61M 2205/3507; A61M 2205/3515; A61N 1/3787; H02J 50/10
See application file for complete search history.

(56) References Cited

U.S. PATENT DOCUMENTS

| | | | |
|---|---|---|---|
| 8,551,163 B2 | 10/2013 | Aber et al. | |
| 8,764,621 B2 | 7/2014 | Badstibner et al. | |
| 2014/0275727 A1 | 9/2014 | Bonde et al. | |
| 2015/0290373 A1 | 10/2015 | Rudser et al. | |
| 2018/0200423 A1 | 7/2018 | Agarwal et al. | |

FOREIGN PATENT DOCUMENTS

WO 2009023905 A1 2/2009

OTHER PUBLICATIONS

International Search Report and Written Opinion of International Application No. PCT/US2021/045293, dated Feb. 25, 2022, 18 pp.

*Primary Examiner* — Jon Eric C Morales
(74) *Attorney, Agent, or Firm* — Shumaker & Sieffert, P.A.

(57) ABSTRACT

An external power transmitter of an implanted medical device system such as a left ventricular assist device (LVAD) system and a method therefore are provided. According to one aspect, a method includes transitioning from applying a first external coil current limit to applying a second external coil current limit to limit current of an external coil coupled to the external power transmitter, the transitioning being based on at least one of an intent to enter a free mode of operation of the implanted medical device system, an existence of an alarm condition, and an existence of transcutaneous energy transfer system (TETS) power transfer.

20 Claims, 6 Drawing Sheets

MANAGING THE ELECTRIC FIELD EXPOSURE IN A FULLY IMPLANTED LVAD SYSTEM

CROSS-REFERENCE TO RELATED APPLICATION n/a

FIELD

The present technology is generally related to implanted medical devices such as a left ventricular assist device (LVAD), and more particularly to limiting current in an external coil configured to inductively transfer power to an internal coil of an implanted medical device.

BACKGROUND

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 16 of the i-controller 14 and to power the LVAD pump 12. The coils 18 and 20 transfer power by mutual induction of electromagnetic energy over the air and through the body. The power supplied by the external power transmitter 21 may come from the detachable battery 24 or from a wall outlet, for example. The transcutaneous energy transmission system (TETS) of a fully implanted LVAD system creates an electromagnetic field with a strength that depends on the power demand of the implanted system, the efficiency of the design, and the relative alignment of the internal and external coils.

SUMMARY

The techniques of this disclosure generally relate to limiting current in an external coil configured to inductively transfer power to an internal coil of an implanted medical device.

According to one aspect, an external power transmitter of an implanted medical device system includes processing circuitry configured to transition from applying a first external coil current limit to applying a second external coil current limit to limit current of an external coil coupled to the external power transmitter, the transition being based on at least one of an intent to enter a free mode of operation of the implanted medical device system, an existence of an alarm condition, and an existence of transcutaneous energy transfer system (TETS) power transfer.

According to this aspect, in some embodiments, the transition is from applying a low coil current limit to applying a high coil current limit at an onset of TETS power regulation, when a timer expires, or when an alarm condition exists. In some embodiments, the processing circuitry is further configured to apply the high coil current limit at a time of starting an internal device of the implanted medical device system. In some embodiments, the transition is from applying a high coil current limit to applying a low coil current limit when an intent to enter the free mode of operation is signaled and there are no current alarms, or when there is a loss in TETS power regulation. In some embodiments, an alarm condition includes at least one of a high power alarm and a device-stopped alarm. In some embodiments, the processing circuitry is further configured to periodically search for an internal coil that aligns with the external coil. In some embodiments, periodically searching includes transmitting search pulses at a first rate when a first condition of a first set of conditions exists and at a second rate otherwise, the first rate being faster than the second rate. In some embodiments, the first set of conditions includes at least one of loss of TETS power regulation and an existence of radio frequency (RF) communication between the external power transmitter and an internal controller of the implanted medical device system. In some embodiments, the processing circuitry is further configured to disable TETS power transfer in an event of the external coil being inaccessible to the external power transmitter. In some embodiments, the processing circuitry is further configured to disable TETS power transfer in an event of external power being unavailable to the external power transmitter.

According to another aspect, a method in an external power transmitter of an implanted medical device system is provided. The method includes transitioning from applying a first external coil current limit to applying a second external coil current limit to limit current of an external coil coupled to the external power transmitter, the transitioning being based on at least one of an intent to enter a free mode of operation of the implanted medical device system, an existence of an alarm condition, and an existence of transcutaneous energy transfer system (TETS) power transfer.

According to this aspect, in some embodiments, the transition is from applying a low coil current limit to applying a high coil current limit at an onset of TETS power regulation, when a timer expires, or when an alarm condition exists. In some embodiments, the method further includes applying the high coil current limit at a time of starting an internal device of the implanted medical device system. In some embodiments, the transition is from applying a high coil current limit to applying a low coil current limit when an intent to enter the free mode of operation is signaled and there are no current alarms, or when there is a loss in TETS power regulation. In some embodiments, an alarm condition includes at least one of a high power alarm and a device-stopped alarm. In some embodiments, the method further includes periodically searching for an internal coil that aligns with the external coil. In some embodiments, periodically searching includes transmitting search pulses at a first rate when a first condition of a first set of conditions exists and at a second rate otherwise, the first rate being faster than the second rate. In some embodiments, the first set of conditions includes at least one of loss of TETS power regulation and an existence of radio frequency (RF) communication between the external power transmitter and an internal controller of the implanted medical device system. In some embodiments, the method further includes disabling TETS power transfer in an event of the external coil being inaccessible to the external power transmitter. In some embodiments, the method includes disabling TETS power transfer in an event of external power being unavailable to the external power transmitter.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to limiting current in an external coil configured to inductively transfer power to an internal coil of an implanted medical device.

When current flows through the external coil 20, an electromagnetic field is generated that radiates outward from the external coil 29. Constraining the electromagnetic field is needed to ensure patient safety by, for example, maintaining tissue exposure within prescribed limits and minimize interactions and interference with other implanted devices such as implanted cardioverter defibrillator (ICD) and minimizing stray electromagnetic fields that may affect external objects such as electrical devices. Some embodiments include a method of constraining the electric field by limiting the electric current within the e-coil 20 of an implanted medical device system. Some embodiments provide multiple limits on the external coil current for different conditions.

Figure 1:
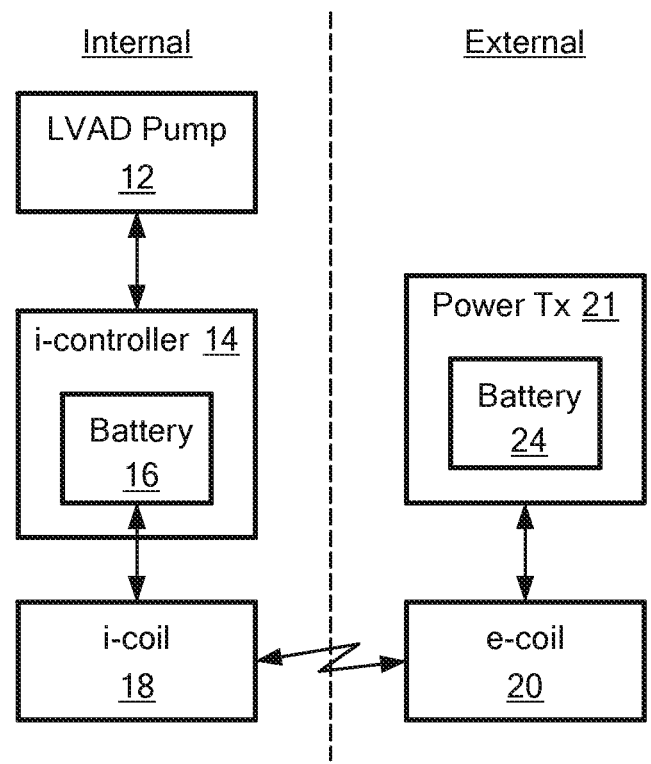
FIG. 1 is a block diagram of an implantable LVAD system.
Figure 2:
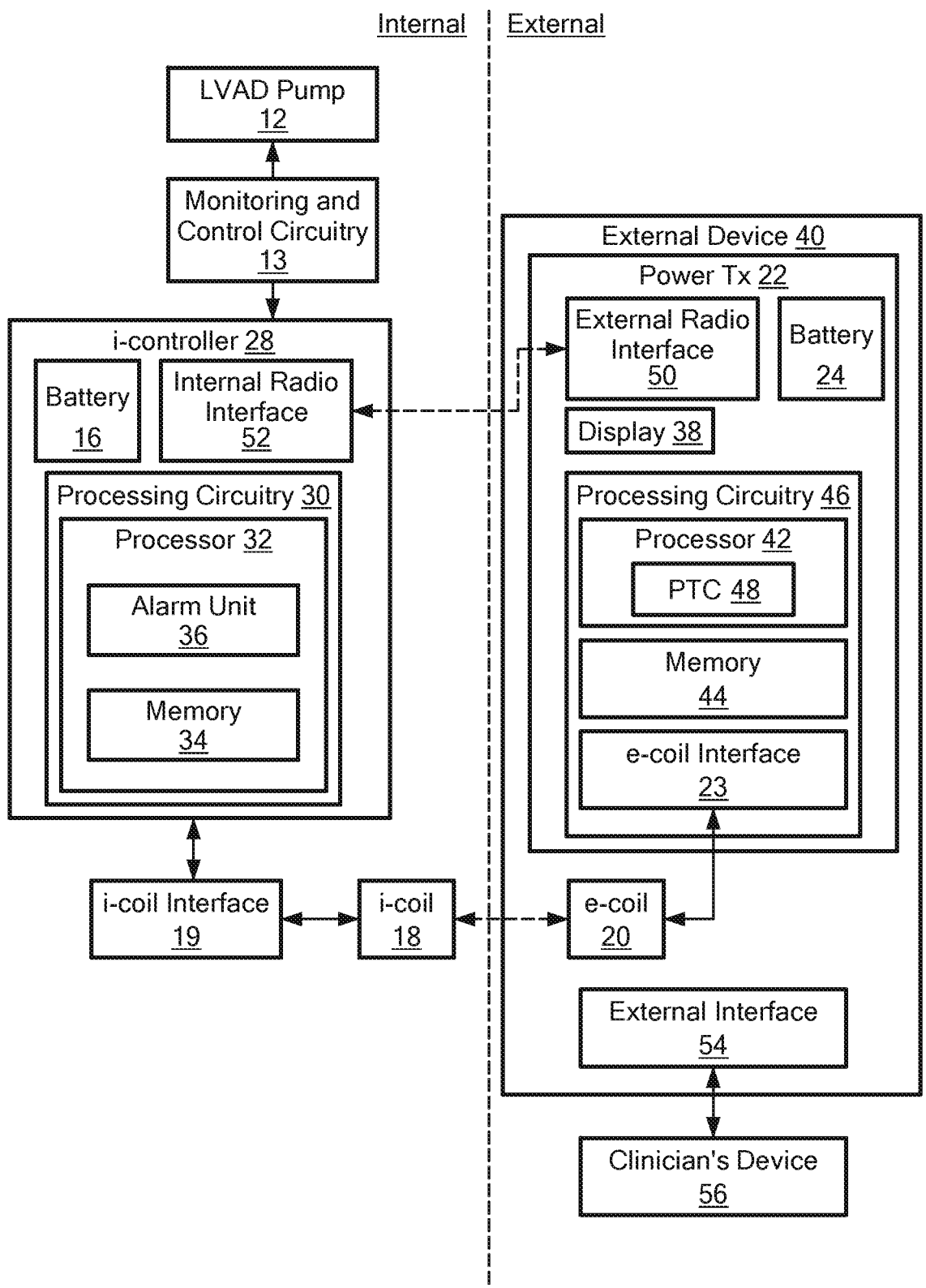
FIG. 2 is a block diagram of an embodiment of an LVAD system that implements a process of limiting current in an external coil configured to inductively transfer power to an internal coil of an implanted medical device.

FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below. The processor 32 may therefore implement an alarm unit 36, which is described below.

A message or result from the alarm unit 36 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42 and may also be configured to store state information concerning a state of the processor 42. The processor 42 may implement a power transfer controller 48 which is described below. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the internal battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the i-controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12. Information obtained from and/or about the LVAD pump 12, such as speed and temperature, may be sent to the external device 40 to be displayed by external display 38.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
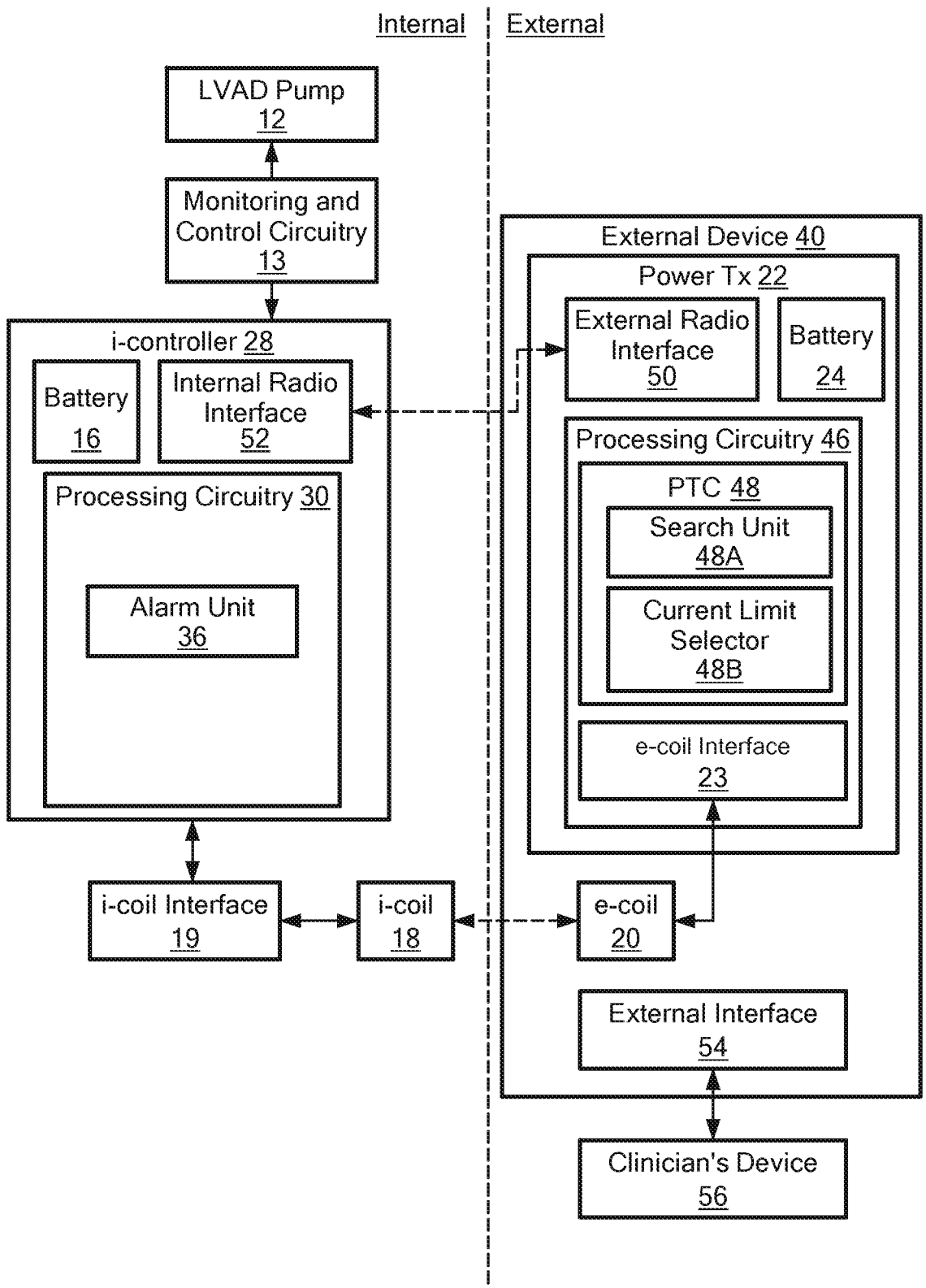
FIG. 3 is a more detailed block diagram of the system shown in FIG. 2 including further detail in relation to the internal alarm unit and the external power transfer controller (PTC)

FIG. 3 is a more detailed block diagram of the system shown in FIG. 2 including further detail in relation to the internal alarm unit 36 and the external power transfer controller (PTC) 48. The alarm unit 36 is configured to generate an alarm signal to be sent to the external power transmitter 22. For instance, if the LVAD pump 12 has stopped, a high power condition is detected, or if a low battery charge status is detected, an alarm signal may be triggered. In the example of FIG. 3, the PTC 48 includes a search unit 48A and a current limit selector 48B. The search unit 48A is configured to search for an i-coil 18 that aligns with the e-coil 20. The current limit selector 48B is configured to limit current applied to the e-coil 20 to one of a plurality of levels.

Figure 4:
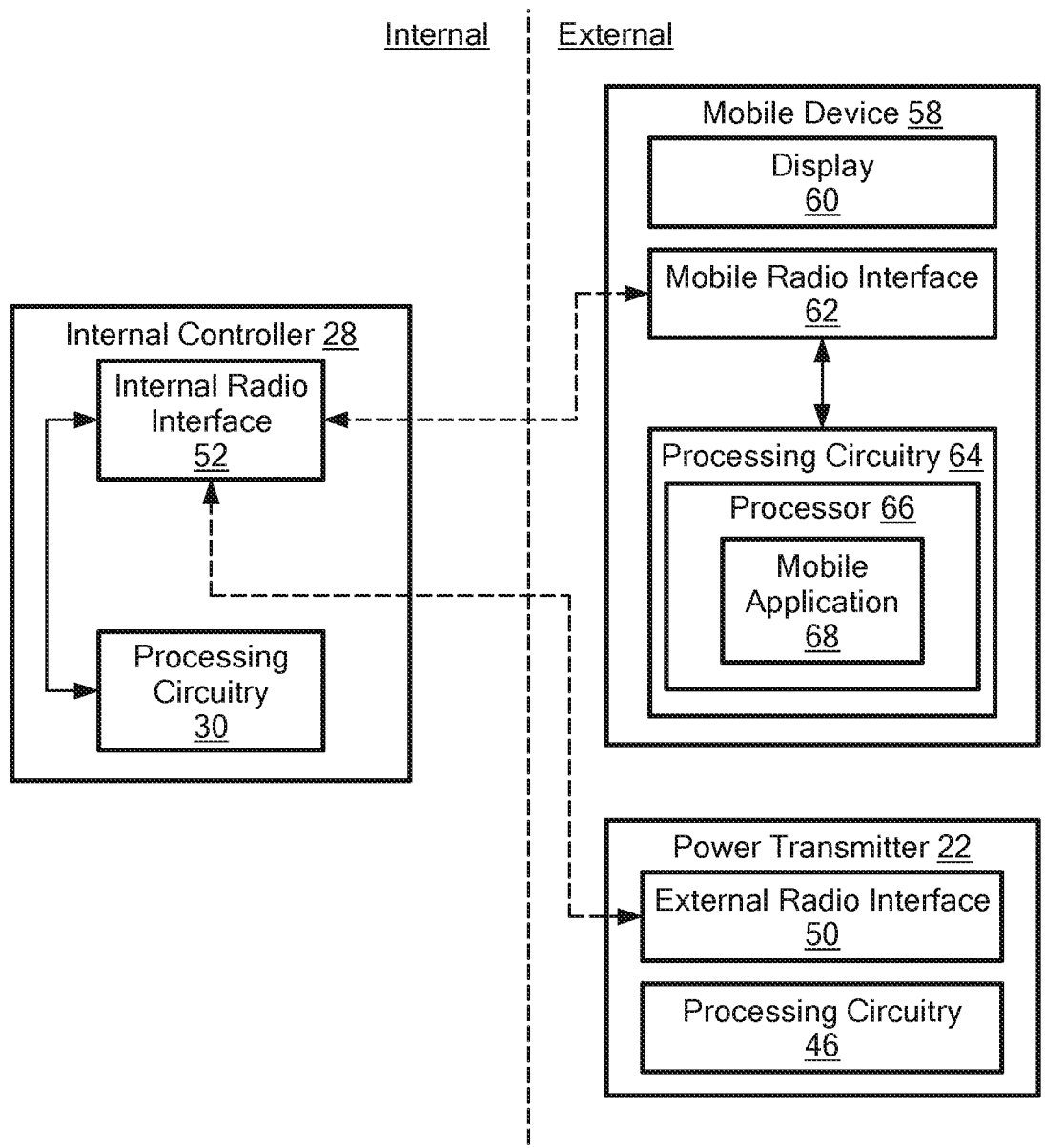
FIG. 4 is a block diagram of an implanted medical device system that includes a mobile device with a mobile application in wireless communication with an internal controller of the implanted medical device.

FIG. 4 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy (BLE) compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements.

Figure 5:
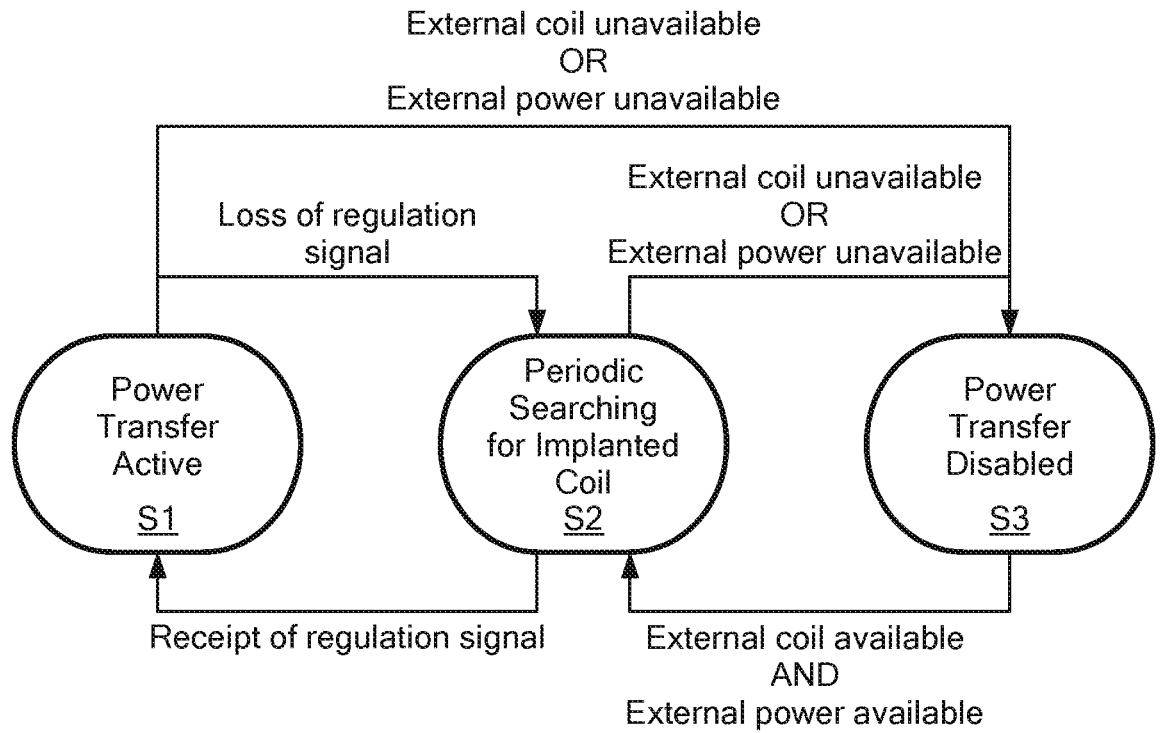
FIG. 5 is a state diagram illustrating three different states of the PTC.

FIG. 5 is a state diagram showings states and transitions between the states as implemented in the processing circuitry 46 of the external power transmitter 22. In State S1, power transfer from the e-coil 20 to the i-coil 18 is actively occurring. In State S2, the search unit 48A of the PTC 48 of processing circuitry 46 of the external power transmitter 22 is periodically searching for the i-coil 18. In State S3, the power transfer from the e-coil 20 to the i-coil 18 is disabled.

Whenever the external detachable battery 24 and e-coil 20 are connected, the external power transmitter 22 will be either actively providing power to the internal components of the implanted medical device system 26 or will be searching for the presence of the i-coil 18 by periodically issuing searching pulses. The periodic searching state allows the rapid onset and recovery of the active power transfer State S1 without requiring significant user intervention. The rate at which search pulses are sent by the external power transmitter 22 may be fast in some cases and slow in others. For example, a fast search pulse rate (for example, once per second) may be used immediately after loss of TETS power regulation or at anytime that RF communication via the radio interfaces 50 and 52 is present. Conversely, a slow search pulse rate (for example, once every ten seconds) may be used at other times to conserve power of the external detachable battery 24.

When in State S1, the power transfer control unit of the processing circuitry 46 of the external power transmitter 22 receives a power regulation signal from the i-controller 28. If there is a loss of the power regulation signal, the PTC 48 transitions from State S1 to State S2 and begins searching for the i-coil 18. Also, when in State S1, if the e-coil 20 becomes unavailable or if external power becomes unavailable, the PTC 48 transitions from State S1 to S3.

"External coil unavailable" refers to a condition in which the e-coil 20 is either disconnected from the external power transmitter 22, or has experienced a continuity fault detected by the external power transmitter 22, such that attempts to provide electrical current to the e-coil 20 will be ineffective. "External power unavailable" refers to a condition in which the external battery 24 is disconnected, fully depleted, or faulted and an external AC or DC source is not connected to the external power transmitter 22.

When in State S2, the search unit 48A of the PTC 48 periodically searches for the i-coil 18. This can be done by applying low current pulses to the e-coil 20. When the e-coil 20 is in proximity to the i-coil 18, the e-coil 20 may receive a power regulation signal from the i-controller 28. When the e-coil 20 receives the power regulation signal, the search unit 48A stops searching for the i-coil 18 and the PTC 48 transitions from State S2 to State S1. When the e-coil 20 is unavailable or the external power is unavailable, then the PTC 48 transitions from State S2 to State S3.

When in State S3, the power transfer is disabled by the PTC 48. When the e-coil 20 becomes available and external power is available, the PTC 48 transitions to State S2.

Figure 6:
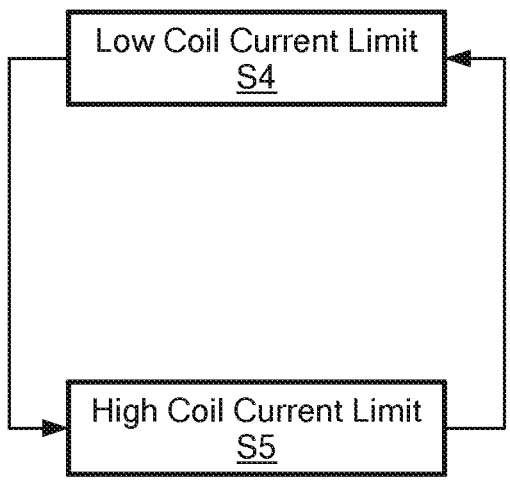
FIG. 6 is a state diagram illustrating two different coil current limit states.

FIG. 6 is a state diagram showing two states: State S4, which is a low coil current limit state and State S5, which is a high coil current limit state. In some embodiments, more than two current limit states may be implemented. In some embodiments, the low coil current limit is set to ensure that all non-alarm power levels are supported without the internal battery 16 charging, which in some embodiments may correspond to an electric field of 35 Vp/m. In some embodiments, the high coil current limit may be set to about 11 Arms, to correspond to an electric field of 120 Vp/m. The States S4 and S5 may be selected by the current limit selector 48B of the PTC 48.

When in the low coil current limit State S4, the PTC 48 may transition to the high coil current limit State S5. This transition may occur at the onset of TETS power regulation, when there is an increase in the amount of power needed by the implantable system, a timeout period for an intent to enter Free Mode has expired, or an alarm is in progress. When in the high coil current limit State S5, the PTC 48 may transition to the low coil current limit State S4. This transition may occur when the intent to enter Free Mode is selected and there are no alarms in progress or when the higher level of delivered power is no longer needed. The Free Mode refers to use of the implanted medical device system 26 without the external device 40 and when the i-controller 28 is powering the LVAD pump 12 and there is no active TETS power transfer. The transition from State S5 to State S4 may occur when there is a loss of TETS communication. In some embodiments, the high coil current limit may also be applied during pump start because the limit constrains not only electric field exposure but also prevents component damage due to high current.

Thus, when the high coil current limit is applied, the following goals may be attained:
  Constraint of electric field exposure to the patient during active power transfer;
  Protection of components from damage due to overcurrent; and
  Minimization of interactions with other implanted devices.

When the low coil current limit is applied, the following goals may be attained:
  Constraint of the electric field exposure to the patient/caregiver or others while not actively transferring power;
  Minimization of interference with nearby equipment;
  Minimization of stray electric fields while the external coil is being removed; and
  Minimization of unintended metal object heating.

An example of an alarm generated by the i-controller 28 that would trigger transition from State S4 to State S5 is a high power alarm or a pump-stopped alarm. Forcing a transition to the high current limit in these cases ensures that maximum power is available as soon as possible after the TETS coils 18 and 20 are coupled to support whatever power demand is present as a result of the alarm.

The onset of TETS regulation refers to the onset of active power transfer between the two coils which warrants a transition to the higher current limit. Conversely, if there is loss of TETS regulation, the low current limit applies as a mechanism to limit the searching pulses. "Intent to enter free mode" refers to a capability of the external power transmitter 22. When the user is about to remove the e-coil 20 to pursue a free mode activity, there is a button on the external power transmitter 22 that may be depressed to prevent the "coils misaligned" notification from occurring. As the user pulls the e-coil 20 away from the i-coil 18, the power transmission efficiency will decrease as the separation distance increases. This may cause the e-coil current to dramatically increase in an attempt to maintain equal power delivery despite the lower efficiency. Under conditions where there is movement of the e-coil 20 relative to the i-coil 18 and the user is not intentionally removing the external coil, this spike in e-coil current would ensure continuous power delivery to the i-coil 18. However, if the user presses the "intent to enter free mode" button indicating that the user will be removing the e-coil 20 intentionally, the PTC 48 applies the low current limit as a way to limit the power spike that in the case of entering the free mode is not needed.

Figure 7:
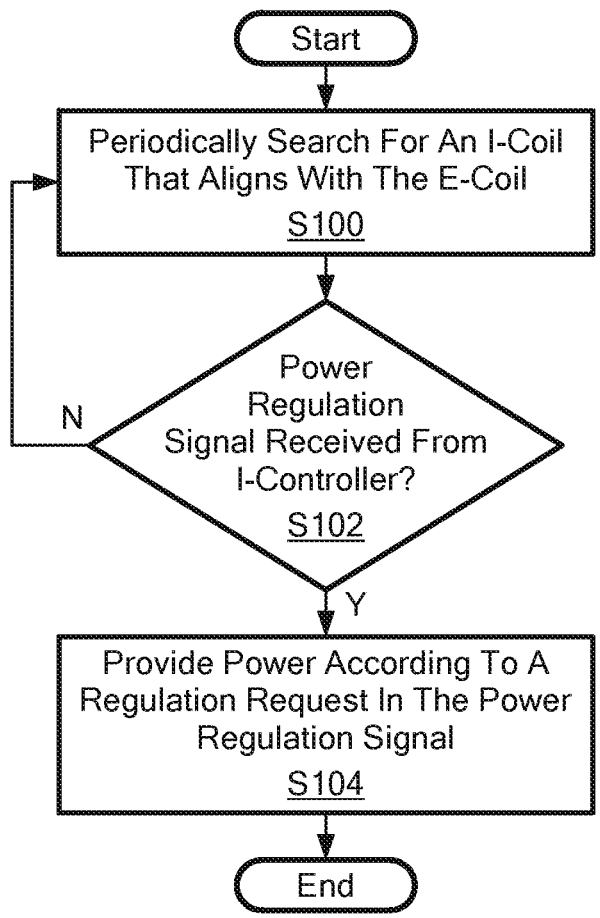
FIG. 7 is flowchart an example process for searching for an internal coil.

FIG. 7 is a flowchart of a process implemented in an external device of an implantable medical device for periodically searching for the i-coil by the search unit 48A of the PTC 48 and for transitioning from the State S2 to the State S1 to actively transfer power to the i-coil 18 via the e-coil 20. When in State S2, the search unit 48A of the PTC 48 periodically searches for an i-coil 18 that aligns with the e-coil 20 (Block S100). A determination is made whether the power regulation signal has been received from the i-controller 28 (Block S102). If not, searching for an i-coil 18 that aligns with the e-coil 20 continues (Block S100). Otherwise, the PTC 48 transitions to State S1 to provide power according to a regulation request in the power regulation signal (Block S104).

Figure 8:
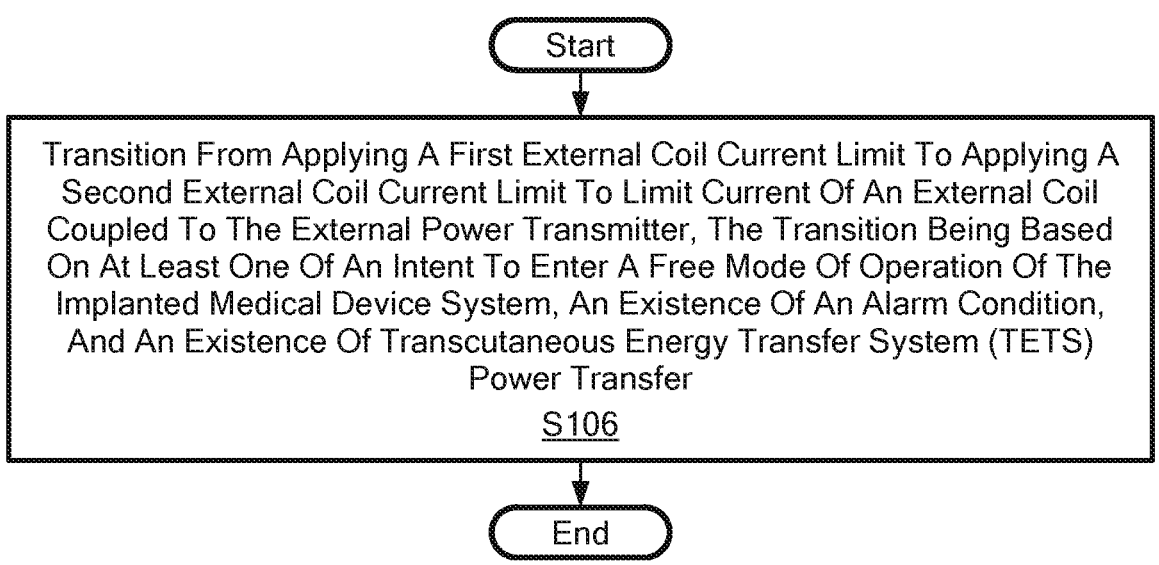
FIG. 8 flowchart of a process implemented in an external power transmitter of an implanted medical device according to principles set forth herein.

FIG. 8 is a flowchart of an example process for transitioning between different states by the PTC 48. The process includes transitioning from applying a first external coil current limit to applying a second external coil current limit to limit current of an external coil coupled to the external power transmitter, the transitioning being based on at least one of an intent to enter a free mode of operation of the implanted medical device system, an existence of an alarm condition, and an existence of transcutaneous energy transfer system (TETS) power transfer (Block S106).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An external power transmitter of an implanted medical device system, the external power transmitter comprising processing circuitry configured to:
    transition from applying a first external coil current limit to applying a second external coil current limit, wherein the first external coil current limit and the second external coil current limit each limit current of an external coil coupled to the external power transmitter, wherein the transition is based on an intent to enter a free mode of operation of the implanted medical device system, and wherein the free mode of operation comprises limiting a power spike associated with an increase in separation distance between the external coil and an internal coil.

2. The external power transmitter of claim 1, wherein the first external coil current limit is a low coil current limit, wherein the second external coil current limit is a high coil current limit, and wherein the processing circuitry is configured to transition by transitioning from applying the first external coil current limit to applying the second external coil current limit in response to an expiration of a timer for the intent to enter the free mode of operation.

3. The external power transmitter of claim 2, wherein the processing circuitry is further configured to apply the second external coil current limit at a time of starting an internal device of the implanted medical device system.

4. The external power transmitter of claim 1, wherein the first external coil current limit is a high coil current limit, wherein the second external coil current limit is a low coil current limit, and wherein the processing circuitry is configured to transition by transitioning from applying the first external coil current limit to applying the second external coil current limit in response to the processing circuitry receiving a signal of the intent to enter the free mode of operation when there are no current alarms.

5. The external power transmitter of claim 1, wherein the processing circuitry is further configured to periodically search for the internal coil that aligns with the external coil.

6. The external power transmitter of claim 5, wherein the periodically searching comprises transmitting search pulses at a first rate when a first condition of a first set of conditions exists and at a second rate otherwise, the first rate being faster than the second rate.

7. The external power transmitter of claim 6, wherein the first set of conditions includes at least one of loss of transcutaneous energy transfer system power regulation and an existence of radio frequency communication between the external power transmitter and an internal controller of the implanted medical device system.

8. The external power transmitter of claim 1, wherein the processing circuitry is further configured to disable transcutaneous energy transfer system power transfer in an event of the external coil being inaccessible to the external power transmitter.

9. The external power transmitter of claim 1, wherein the processing circuitry is further configured to disable transcutaneous energy transfer system power transfer in an event of external power being unavailable to the external power transmitter.

10. The external power transmitter of claim 1, wherein the external power transmitter is configured to send a signal of the intent to enter free mode based on a user input, and wherein the processing circuitry is configured to receive the signal of the intent to enter free mode.

11. A method comprising:
    transitioning, by processing circuitry of an external power transmitter of an implanted medical device system, from applying a first external coil current limit to applying a second external coil current limit, wherein the first external coil current limit and the second external coil current limit each limit current of an external coil coupled to the external power transmitter, wherein the transitioning is based on an intent to enter a free mode of operation of the implanted medical device system, and wherein the free mode of operation comprises limiting a power spike associated with an increase in separation distance between the external coil and an internal coil.

12. The method of claim 11, wherein the first external coil current limit is a low coil current limit, wherein the second external coil current limit is a high coil current limit, and wherein the transitioning comprises transitioning from applying the first external coil current limit to applying the second external coil current limit in response to an expiration of a timer for the intent to enter the free mode of operation.

13. The method of claim 12, further comprising applying, by the processing circuitry, the second external coil current limit at a time of starting an internal device of the implanted medical device system.

14. The method of claim 11, wherein the first external coil current limit is a high coil current limit, wherein the second external coil current limit is a low coil current limit, and wherein the transitioning comprises transitioning from applying the first external coil current limit to applying the second external coil current limit in response to receiving a signal of the intent to enter the free mode of operation when there are no current alarms.

15. The method of claim 11, further comprising periodically searching, by the processing circuitry, for the internal coil that aligns with the external coil.

16. The method of claim 15, wherein the periodically searching comprises transmitting search pulses at a first rate when a first condition of a first set of conditions exists and at a second rate otherwise, the first rate being faster than the second rate.

17. The method of claim 16, wherein the first set of conditions includes at least one of loss of transcutaneous energy transfer system power regulation and an existence of radio frequency communication between the external power transmitter and an internal controller of the implanted medical device system.

18. The method of claim 11, further comprising disabling transcutaneous energy transfer system power transfer in an event of the external coil being inaccessible to the external power transmitter.

19. The method of claim 11, further comprising disabling transcutaneous energy transfer system power transfer in an event of external power being unavailable to the external power transmitter.

20. The method of claim 11, further comprising:

sending, by the external power transmitter, a signal of the intent to enter free mode based on a user input; and receiving, by the processing circuitry, the signal of the intent to enter free mode.

\* \* \* \* \*